(12) United States Patent  (10) Patent No.: US 8,835,415 B2
Bhaskaran et al.  (45) Date of Patent: Sep. 16, 2014

(54) STANDARDIZED COMPOSITION, METHOD OF MANUFACTURE AND USE IN THE RESOLUTION OF RNA VIRUS INFECTION

(75) Inventors: Sunil Bhaskaran, Pune (IN); Mohan Vishwaraman, Pune (IN)

(73) Assignee: Indus Biotech Private Limited, Pune (IN)

( * ) Notice: Subject to any disclaimer, the term of this patent is extended or adjusted under 35 U.S.C. 154(b) by 1366 days.

(21) Appl. No.: 12/566,061

(22) Filed: Sep. 24, 2009

(65) Prior Publication Data

US 2011/0039923 A1  Feb. 17, 2011

(30) Foreign Application Priority Data

Aug. 11, 2009 (IN) ...................... 01857/MUM/2009

(51) Int. Cl.
*A61K 31/395* (2006.01)
*A61K 31/353* (2006.01)
*A61K 36/77* (2006.01)
*A61K 36/54* (2006.01)
*A61K 36/48* (2006.01)

(52) U.S. Cl.
CPC ............... *A61K 31/353* (2013.01); *A61K 36/77* (2013.01); *A61K 36/54* (2013.01); *A61K 36/48* (2013.01)
USPC ........................................................ 514/183

(58) Field of Classification Search
None
See application file for complete search history.

(56) References Cited

U.S. PATENT DOCUMENTS

| 6,610,320 B2 * | 8/2003 | Schmitz et al. ............... 424/440 |
| 6,638,971 B2 * | 10/2003 | Romanczyk et al. ......... 514/456 |
| 2005/0202041 A1 * | 9/2005 | McDougald et al. ...... 424/202.1 |

OTHER PUBLICATIONS

Kenny, T.P. et al., Exp. Biol. Med. (Maywood), 2004, 229:255.*

* cited by examiner

*Primary Examiner* — San-Ming Hui
*Assistant Examiner* — Jeanmarie Calvillo
(74) *Attorney, Agent, or Firm* — Harness, Dickey & Pierce, PLC (57) ABSTRACT

The present disclosure is in relation to antiviral preparations obtained from plant sources namely *Cinnamon*, *Litchi* and *Arachis*. It provides a composition and a process to prepare the composition comprising pentameric procyanidin flavonoid, trimers and tetramers. The composition improves immunity response and found to be useful in treatment and management of HIV infection and AIDS and for the prevention, treatment and management of Influenza virus and infection.

34 Claims, 5 Drawing Sheets
(1 of 5 Drawing Sheet(s) Filed in Color)

STANDARDIZED COMPOSITION, METHOD OF MANUFACTURE AND USE IN THE RESOLUTION OF RNA VIRUS INFECTION

FIELD

The present disclosure is related to antiviral preparations. The disclosure provides antiviral preparations obtained from plants and which improves immune response and are found to be effective against HIV infection, AIDS and Influenza virus and infection.

BACKGROUND

Catechins are polyphenolic plant metabolites which belong to the flavonoid family. The molecular formula and weight of catechins are $C_{15}H_{14}O_6$ and 290 g/mol. Catechin and epicatechin are epimers, with (−)-epicatechin and (+)-catechin being the most common optical isomers found in nature.

Procyanidins or condensed tannins are flavonoid oligomers whose building blocks are (+)-catechin and (−)-epicatechin. They are oligomeric end products of the flavonoid biosynthetic pathway and are now identified and recognised for their beneficial effects in human beings. They are present abundantly in the plant kingdom in fruits, barks, leaves and seeds where they provide protection against light, oxidation and predators. Procyanidins are found in many plants, mainly apples, pine bark, cinnamon bark, *litchi* pericarp, peanuts, grape seed, cocoa, grape skin, bilberry, cranberry, black currant, green tea and black tea.

Based on the linkage between the successive monomeric units, procyanidins are classified as Types A, B or C polyphenols.

Generally the linkage between successive monomeric units of procyanidins is between the $4^{th}$ position of the 'upper' unit and the $8^{th}$ position of the 'lower' unit, leading to a Type B procyanidin. Alternatively, the linkage can occur between $C_4$ of the 'upper' unit and $C_6$ of the lower unit, leading to a Type C procyanidin. Type B and C polyphenols are abundantly seen in many botanical sources. When successive monomeric units are linked by an ether linkage between the C2 and C4 of the 'upper' unit and the oxygen at the C7 position and the $C^6/C^8$ positions (respectively) of the lower unit, a Type A procyanidin is formed. Type A procyanidins are seen rarely when compared to Type B and C polyphenols.

Immunological Response to an Antigen

The immune system is a collection of mechanisms within a host that protects it against diseases by identifying and eliminating the pathogen. The system's response to a pathogen starts from the identification of a foreign protein to finally destroying the source of this foreign protein thereby protecting the host. Even the recognition of a simple protein from unicellular organism involves a series of complex steps which lead to the final elimination of the organism from the host. This entire process is the immunological response to the presence of a foreign protein or the antigen.

Resolution of infection by the immune system is the immunological response to the antigen, and it can be divided into 3 stages:

Activation and Mobilization: White Blood Cells (WBCs) are activated when they identify a foreign molecule or an antigen. Immune cells like macrophages and T cells release substances that attract other immune cells to the site of foreign molecule identified and thus mobilize the myriad of immune cells to eradicate the pathogen.

Regulation: The elicited immune response must be controlled in order to prevent excessive damage to the host. Regulator T-lymphocytes facilitate the control of the immune responses by secreting cytokines which act as the messengers of the immune system and thus regulate an exaggerated immune response.

Resolution: Infection resolution involves confining the pathogen and eliminating it from the body. After the pathogen is eliminated, most of the WBCs are destroyed, those that remain are called 'memory cells' and protect the host against future infection by the same pathogen by eliciting an early immune response to the pathogen.

A pathogen succeeds in causing an infection when the host is unable to surmount a defense strong enough to eliminate the pathogen. In such cases the antibodies produced by the host are insufficient to neutralize the existing numbers of the antigen. Hence the free antigens succeed in infecting the host. In such cases, external aids like antibiotics and antivirals are used to reduce the numbers of the antigen. Once the antigen numbers are reduced, the immunologic response is sufficient to eliminate the pathogen.

HIV Infection and AIDS:

Human immunodeficiency virus (HIV) is a retrovirus that destroys the immune system. This infection can eventually lead to Acquired Immunodeficiency Syndrome (AIDS), a serious and life-threatening condition in which the immune system fails to work properly. HIV primarily infects specific cells in the human immune system: "helper" T-lymphocytes (specifically $CD4^+$ T cells), macrophages and dendritic cells. When $CD4^+$ T cell numbers decline below a critical level, cell-mediated immunity is lost, and the body becomes progressively more susceptible to opportunistic infections.

HIV Life Cycle: Once HIV has entered the host, HIV needs specific host cells to facilitate its replication and propagation. The host cell in the case of HIV is the T-cell or CD4 cell.

1. Recognition of host and binding: HIV seeks out CD4 cells and attaches to them by way of a "lock and key" system via coreceptors on the cell surface. Proteins on the surface of HIV attach to complimentary proteins on the CD4 cell.

2. Attachment and entry into host: After attachment, the HIV injects viral proteins into the cellular fluids (cytoplasm) of the T-cell. This causes a fusion of the cell membrane to the outer envelope of the HIV.

3. Disassembly of viral proteins: In order to use its genetic material (RNA) for reproduction, the protective coating surrounding the RNA must be dissolved. Without this step, conversion of RNA to DNA (the building blocks of new HIV copies) cannot take place, and replication is halted.

4. Reverse transcription: Once inside the cell, the single stranded RNA of the HIV must be converted to the double stranded DNA. This step is brought about by the enzyme reverse transcriptase. Reverse transcriptase uses building blocks from the T-cell to help convert the viral RNA to DNA. The DNA contains the genetic information needed for HIV replication.

5. Replication and assembly into new virion: In order to replicate, the newly formed viral DNA must integrate into the host nucleus. This process is not entirely understood yet, but is believed to be aided by viral transport proteins. On integration, the virus gestates while the host cell prepares the proteins it requires to complete replication. Once the materials are available, they are cleaved by the virus based on requirement and structure and are subsequently assembled into new HIV. This process is aided by the protease enzyme.

6. Budding off from host cell: The final step of the viral replication cycle is called budding. With its genetic material tucked away and a new outer coat made from the host CD4 cell's membrane, the newly formed HIV pinches off and enters into circulation, ready to start the whole process again.

Current Interventions:

The current methods of interrupting HIV replication and propagation include: virus entry inhibitors; membrane fusion Inhibitors; and reverse transcriptase inhibitors; integrase inhibitors; protease inhibitors; maturation inhibitors, etc. The FDA has approved a number of drugs for treating HIV infection. Most of these drugs work by their antiretroviral (ARV) mechanism of action.

Infection with the Human Immunodeficiency Virus (HIV) presents political, economic, public health, social and scientific challenges to nations worldwide. At the close of 2007, an estimated 33.2 million people were living with HIV/AIDS worldwide. Hence there is an urgent need for the management and/or treatment of this disease with safer and more efficacious drugs. An additional challenge presented by this virus is its susceptibility to mutation. The viral proteins of HIV are prone to mutation and hence drug resistant strains pose an additional threat which creates a need for newer classes of drugs.

Influenza Virus:

Influenza is an infectious disease caused by RNA viruses of the family Orthomyxoviridae (the influenza viruses), that affects birds and mammals. Infection by this virus affects mainly the nose, throat, bronchi and, occasionally, lungs.

Structure of the Influenza Virus: The Influenza virus is classified into 3 categories: Influenza virus A, B and C. The 3 subtypes of influenza viruses have a very similar overall structure. The viruses are made of a viral envelope containing two main types of glycoproteins which are wrapped around a central core. The central core contains the viral RNA genome and other viral proteins that package and protect this RNA. Hemagglutinin (HA) and neuraminidase (NA) are the two large glycoproteins on the outside of the viral particles.

Influenza Virus A: The type A viruses are the most virulent human pathogens among the three influenza types and cause the most severe disease. The influenza A virus can be subdivided into different serotypes based on the antibody response to these viruses. The serotypes that have been confirmed in humans, ordered by the number of known human pandemic deaths, are: H1N1, H2N2, H3N2, H5N1, H7N7, H1N2, H9N2, H7N2, H7N3, H10N7. Influenza A viruses have caused several pandemics during the last century, and continue to cause annual epidemics. The emergence of new strains of influenza continues to pose challenges to public health and scientific communities. The H1N1 virus is a serotype of the Influenza A virus and is one of the most virulent strains known to affect human beings. The H1N1 serotype has been responsible for millions of deaths in 1918 (Spanish Flu) and is more recently causing a Swine Flu global pandemic.

Influenza Viral Life Cycle: The influenza viral replication and propagation process is outlined below:

1. Recognition of host and binding: Binding of the virus to the host cell using the HA protein to sialic acid bound to sugars on the surfaces of epithelial cells. Epithelial cells are typically present in the nose, throat and lungs of mammals and in the intestines of birds 2. Attachment and entry into host: After the binding, the HA protein is cleaved off and the virus enters the cell by endocytosis.

3. Disassembly of viral proteins: Once the virus enters the cell, the pH and ambient conditions of the endosome lead to:
 a. A part of HA fusing the viral envelope to the vacuole membrane
 b. The M2 ion channel permits the entry of protons to the viral core which acidify the viral core leading to its disassembly and the subsequent release of the viral RNA and core proteins into the host cell cytoplasm 4. Reverse transcription: The viral RNA and core proteins are now transported into the cell nucleus where the RNA is transcribed and further translated into viral proteins.

5. Budding off from host cell: HA and NA proteins form clusters near the cell membrane which subsequently also house the viral RNA and core proteins, which then lead to 'budding' of the virus and propagation for subsequent infection.

As seen from the infection and propagation steps detailed above HA and NA play an important role in infection. Before release of the virion, NA also cleaves sialic acid so as to prevent the binding of HA to sialic acid.

Current Interventions for Influenza A virus: There are two classes of drugs approved by the United States FDA against the Influenza A virus: Ion channel inhibitors like Adamantanes (amantadine hydrochloride and rimantadine); and Neuraminidase inhibitors like Oseltamivir (TAMIFLU) and Zanamivir (RELENZA)

The Influenza A virus is prone to mutations. These mutations are primarily of viral proteins like NA, HA and M2 ion channel proteins, and hence inhibitors of these proteins will be ineffective against mutant strains. The mutation potential and the 2009 Influenza A global pandemic presents an urgent need for therapies which offer a treatment and prevention options against this virus.

PRIOR ART

Richard Anderson et al, "*Isolation and characterization of polyphenols Type A polymers from cinnamon with insulin-like biological activity*" in the Journal of Agricultural and Food Chemistry, 2004, pp 52, 65-70.

This paper describes an aqueous extract of commercial cinnamon and has identified polyphenolic polymers that increase glucose metabolism by roughly 20 fold in in vitro cell lines. They have used *Cinnamomum cassia* (*Korintji cassia*) for the preparation of this extract. This variety has a high content of coumarin and cinnamaldehyde.

This paper further describes a preparatory HPLC method for the preparation and characterization of this aqueous extract.

This publication describes A-type doubly linked procyanidin of catechins. This paper has identified trimer (molecular weight 864), tetramer (molecular weight 1152) and oligomer of catechins that are isolated from cinnamon.

Kilkuskie et al, "*HIV and reverse transcriptase inhibition by tannins*" in the Bioorqanic and Medicinal Chemistry Letters, 1992, Vol 2, pp 1529-1534.

This publication evaluates tannins and condensed tannins for their anti-HIV activity and their potential to inhibit the reverse transcriptase enzyme. Although this study discovered some tannins with anti-HIV activity, they were burdened with the associated toxicities. This publication talks about 3 compounds which are condensed forms of catechins. Molecules 40, 44 and 45 are dimers, trimers and tetramers of catechins. This paper concluded that there was no correlation between the inhibition of the RT enzyme and the anti-HIV action of these tannins. Additionally, Molecules 44 and 45 showed an anti-HIV activity of 90% and 73% respectively, but did not show significant inhibition of the RT enzyme.

Michael Ovadia et al. in Patent Application US 2006 275515A1

This patent titled "Anti-viral preparations obtained from a natural cinnamon extract" have described a natural aqueous extract obtained from cinnamon having anti-viral properties. This document describes a water extract of cinnamon which is subjected to salting out precipitation with a salt. This precipitate is redissolved in water or buffer and purified using sepharose chromatography and subsequently eluted with another buffer and galactose.

The commonly used process of salting out refers to the selection of high molecular weight molecules (usually peptides). Hence it is quite evident from this process that the process described in this document is aimed at recovering high molecular weight molecules (about 10 Kda).

The active ingredient of the composition as per the claim is having a molecular weight more than 10 KDA and it responds to an absorbance at 280 nm at between about 15 and 20OD. This compound is finally eluted from the sepharon column using phosphate buffer and galactose. Therefore, the final compound will have high concentrations of phosphates and galactose.

This high molecular weight compound described in this application has been tested in influenza A PR 8 virus, Para Influenza (Sendai) virus, Pre-absorption into erythrocytes and weight gain in mice infected with influenza or the sendai virus and an HIV syncytia study.

Example 13 of this patent application describes a test done with this extract in MT2 cells to check the effect on Syncytia formation. As per FIG. 15 of this application at concentrations of 60 to 100 micrograms, it inhibits syncytia formation. Syncytia formation is not a confirmatory test for anti-viral activity. This is elucidated with evidence in the following publication. [Gueseppe pantaleo et al Eur J immunology 1991, 21, 1771:1774 dissociation between syncytia formation and HIV spreading. Suppressing Syncytia formation does not necessarily reflect inhibition of HIV infection.]

Although, the disclosed extract showed potential to inhibit syncytia formation, it should be noted that only some strains of HIV cause syncytia formation. Additionally syncytia formation cannot be linked to the presence or to the progression of HIV infection or AIDS. Syncytia formation is merely a phenotype that may be expressed by some strains. Lack of syncytia formation cannot be linked to the absence of HIV or to the management of the infection.

SUMMARY

Objectives of Disclosure

First objective of the disclosure is to provide a composition comprising pentameric procyanidin flavonoid, trimer and tetramer from plant source.

Second objective of the disclosure is to provide a process to prepare composition comprising pentameric procyanidin flavonoid, trimer and tetramer from plant sources such as *Cinnamomum, Litchi* and *Arachis.*

Third objective of the disclosure is to provide a composition which improves immune response in subjects and also which are effective against HIV infection, AIDS and Influenza virus and infection.

Statement Of Disclosure

Accordingly, the present disclosure is in relation to a composition comprising pentameric procyanidin flavonoid of concentration ranging from about 55% w/w to about 99% w/w, trimers and tetramers each at a concentration ranging from about 0.5% w/w to about 35% w/w, optionally along with pharmaceutically acceptable excipients; a process for preparation of composition comprising pentameric procyanidin flavonoid of concentration ranging from about 55% w/w to about 99% w/w, trimers and tetramers each at a concentration ranging from about 0.5% w/w to about 35% w/w, said process comprising steps of extracting pulverized plant mass using organic solvent to remove toxic substances; drying the mass to remove the organic solvent; re-extracting the dried mass using aqueous solvent to obtain extract; and purifying the extract through chromatographic column followed by concentrating, purifying, standardizing and drying to obtain the composition; a method to improve immunological response in a subject in need thereof, said method comprising step of administering pharmaceutically effective amount of composition comprising pentameric procyanidin flavonoid of concentration ranging from about 55% w/w to about 99% w/w, trimers and tetramers each at a concentration ranging from about 0.5% w/w to about 35% w/w, optionally along with pharmaceutically acceptable excipients to the subject; and a method of treating, preventing and managing retroviral infections in a subject in need thereof, said method comprising step of administering pharmaceutically effective amount of composition comprising pentameric procyanidin flavonoid of concentration ranging from about 55% w/w to about 99% w/w, trimers and tetramers each at a concentration ranging from about 0.5% w/w to about 35% w/w, optionally along with pharmaceutically acceptable excipients to the subject.

DRAWINGS

The file of this patent or application file contains at least one drawing executed in color. Copies of this patent or patent application publication with color drawings will be provided by the Patent and Trademark Office upon request and payment of necessary fee.

FIG. 1 shows molecular structure of Pentamer of Falvonoid;

FIG. 2 shows El-MS of Pentameric Pentamer of Falvonoid;

FIG. 3 shows 13C NMR of Pentamer of Falvonoid;

FIG. 4 shows flash Chromatography of composition to identify Pentamer of Falvonoid; and FIG. 5 shows HPLC of Pentamer of Falvonoid.

DETAILED DESCRIPTION

The present disclosure is in relation to a composition comprising pentameric procyanidin flavonoid of concentration ranging from about 55% w/w to about 99% w/w, trimers and tetramers each at a concentration ranging from about 0.5% w/w to about 35% w/w, optionally along with pharmaceutically acceptable excipients.

In one embodiment of the present disclosure, composition is obtained from plant source selected from a group comprising *Cinnamomum, Litchi* and *Arachis.*

In another embodiment of the present disclosure the preferable concentration of pentameric procyanidin flavonoid is ranging from about 80 w/w to about 99% w/w, trimers and tetramers each at a concentration ranging from about 0.5% w/w to about 20% w/w.

In another embodiment of the present disclosure said pentameric procyanidin flavonoid is having molecular weight of about 1440.

In another embodiment of the present disclosure said pentamer is type A procyanidin pentamer.

In another embodiment of the present disclosure said excipients are selected from a group comprising gums, granulating agents, binding agents, lubricating agents, disintegrating agents, sweetening agents, coloring agents, flavoring agents, coating agents, plasticizers, preservatives, suspending agents, emulsifying agents, antistatic agents, and spheronization agents.

In another embodiment of the present disclosure said composition is formulated into various dosage forms selected from a group comprising tablet, troches, lozenges, aqueous or oily suspensions, dispersible powders or granules, emulsion in hard or soft gel capsules, syrups and elixirs.

The present disclosure is in relation to a process for preparation of composition comprising pentameric procyanidin flavonoid of concentration ranging from about 55% w/w to about 99% w/w, trimers and tetramers each at a concentration ranging from about 0.5% w/w to about 35% w/w, said process comprising steps of extracting pulverized plant mass using organic solvent to remove toxic substances; drying the mass to remove the organic solvent; re-extracting the dried mass using aqueous solvent to obtain extract; and purifying the extract through chromatographic column followed by concentrating, purifying, standardizing and drying to obtain the composition.

In embodiment of the present disclosure the pulverized plant mass is selected from a group of plants comprising *Cinnamomum, Litchi* and *Arachis*.

In another embodiment of the present disclosure the organic solvent is selected from a group comprising ethylacetate, butylacetate, amylacetate, 2-ethylhexylacetate and any combinations thereof.

In another embodiment of the present disclosure said extraction is carried out for a time period ranging from about 8 hours to about 12 hours, preferably for about 10 hours.

In another embodiment of the present disclosure said toxic substances include coumarin and aldehydes.

In another embodiment of the present disclosure said extract is filtered through two stage chromatographic column.

In another embodiment of the present disclosure said chromatographic columns are selected from a group comprising XAD-1180, XAD-7HP and XAD-1140 resins.

In another embodiment of the present disclosure said re-extraction with aqueous solvent is carried out at a pH ranging from about 3.8 to about 5.8, preferably at about 4.0

In another embodiment of the present disclosure said re-extraction is carried out for a time period ranging from about 8 hours to about 12 hours, preferably for about 10 hours at a temperature ranging from about 30° C. to 90° C., preferably ranging between 31° C. to 40° C.

In another embodiment of the present disclosure said aqueous solvent is acidified deionised water.

In another embodiment of the present disclosure said composition further comprising of excipients selected from a group comprising gums, granulating agents, binding agents, lubricating agents, disintegrating agents, sweetening agents, coloring agents, flavoring agents, coating agents, plasticizers, preservatives, suspending agents, emulsifying agents, antistatic agents, and spheronization agents.

The present disclosure is in relation to a method to improve immunological response in a subject in need thereof, said method comprising step of administering pharmaceutically effective amount of composition comprising pentameric procyanidin flavonoid of concentration ranging from about 55% w/w to about 99% w/w, trimers and tetramers each at a concentration ranging from about 0.5% w/w to about 35% w/w, optionally along with pharmaceutically acceptable excipients to the subject.

In another embodiment of the present disclosure the immunological response is improved in diseases selected from a group but not limiting to influenza, HIV infection and AIDS.

In another embodiment of the present disclosure the immunological response is improved in a subject in need thereof.

In another embodiment of the present disclosure the pharmaceutically effective amount of composition is ranging from about 1 mg/kg to about 100 mg/kg body weight of the subject.

In another embodiment of the present disclosure said method is used in treatment, prevention and management of infection caused by a pathogen in the subject.

In another embodiment of the present disclosure said pathogen includes influenza A virus and HIV viruses.

In another embodiment of the present disclosure said virus types are H1N1, H3N2, X4 and R5 tropic virus.

In another embodiment of the present disclosure the subject is an animal or human being.

The present disclosure is in relation to a method of treating, preventing and managing viral infections in a subject in need thereof, wherein said method comprising step of administering pharmaceutically effective amount of a composition comprising pentameric procyanidin flavonoid of concentration ranging from about 55% w/w to about 99% w/w, trimers and tetramers each at a concentration ranging from about 0.5% w/w to about 35% w/w, optionally along with pharmaceutically acceptable excipients as an antiviral preparation to the subject.

In another embodiment of the present disclosure said composition inhibits influenza A virus, X4 tropic and R5 tropic virus of HIV.

In another embodiment of the present disclosure the pharmaceutically effective amount of composition is ranging from about 1 mg/kg to about 100 mg/kg body weight of the subject.

In another embodiment of the present disclosure the subject is an animal or human being.

The present disclosure is in relation to a method of treating, preventing and managing retroviral infections in a subject in need thereof, said method comprising step of administering pharmaceutically effective amount of composition comprising pentameric procyanidin flavonoid of concentration ranging from about 55% w/w to about 99% w/w, trimers and tetramers each at a concentration ranging from about 0.5% w/w to about 35% w/w, optionally along with pharmaceutically acceptable excipients to the subject.

In embodiment of the present disclosure said retroviral infections include influenza A infection and HIV infection and AIDS.

In another embodiment of the present disclosure the pharmaceutically effective amount of composition is ranging from about 1 mg/kg to about 100 mg/kg body weight of the subject.

In another embodiment of the present disclosure the subject is an animal or human being.

Figure 1:
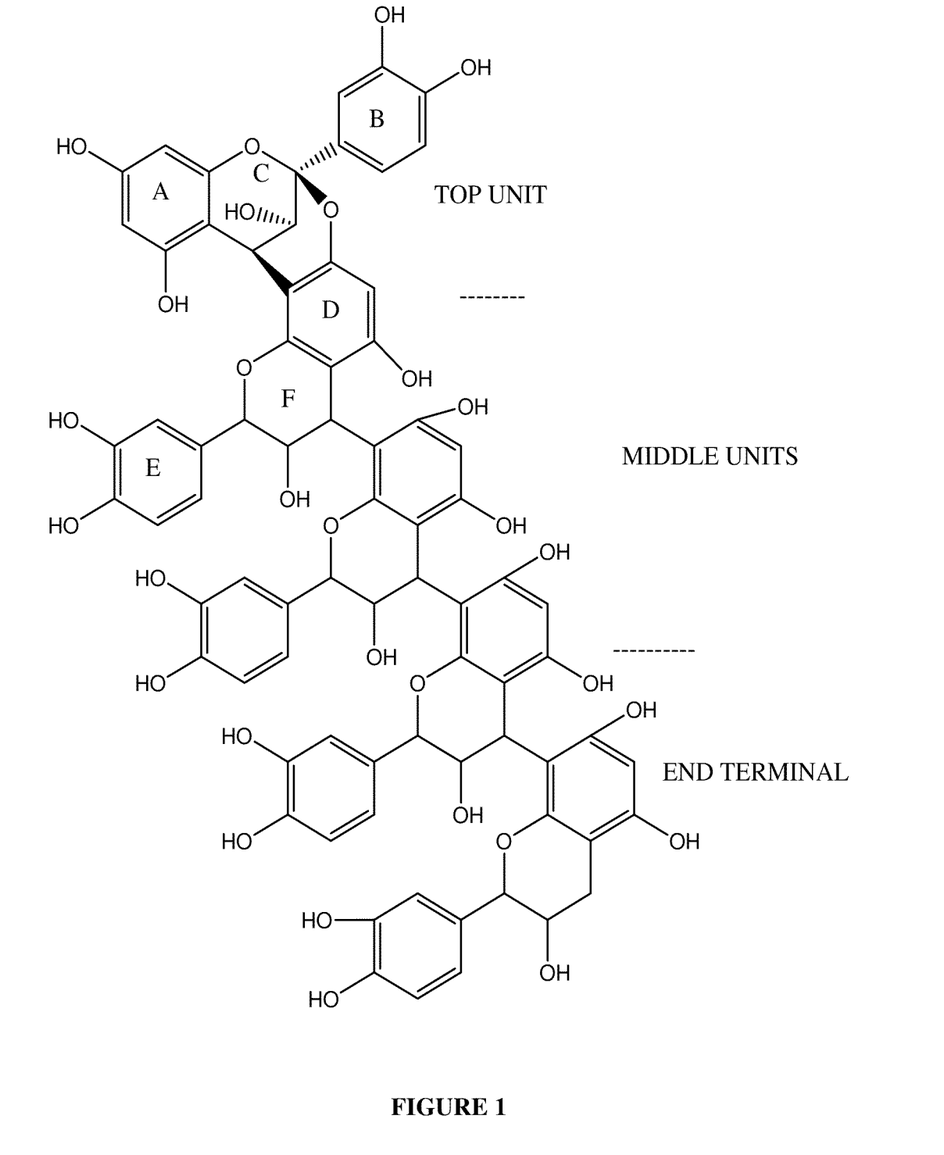

The present disclosure relates to a novel standardized composition derived from botanical sources, standardized to 50% to 99% of a Type A procyanidin pentamer of a flavanoid as shown in FIG. 1. The present disclosure also relates to a method of obtaining a novel standardized composition derived from botanical sources, standardized to 50% to 99% of a Type A procyanidin pentamer of a flavonoid. The present disclosure also relates to the use of a novel standardized composition derived from botanical sources, standardized to 50% to 99% of a Type A procyanidin pentamer of a flavanoid for the prevention, treatment and management of HIV and influenza infection.

The present disclosure also relates to the use of a novel standardized composition derived from botanical sources, standardized to 50% to 99% of a Type A procyanidin pentamer of a flavanoid to elicit an improved immunological response to an antigen in a subject in need thereof.

In another embodiment of the present disclosure, the immunological response can be treatment, management or prophylactic in nature In one embodiment of the present disclosure the botanical sources used to obtain the composition are the *Cinnamomum, Litchi* and *Arachis*.

In one embodiment of the present disclosure, the novel standardized composition derived from botanical sources is standardized to a Type A procyanidin pentamer of flavanoid.

In another embodiment of the present disclosure, the pentamer has a molecular weight of 1440 as shown in FIG. 1.

In another embodiment of the present disclosure, the composition comprises a pentamer ranging from 50% to 99%.

In another embodiment of the present disclosure, the composition comprises trimer and tetramer ranging from 1% to 35%.

In another embodiment of the present disclosure, the composition is as characterized by the chromatogram in FIG. 5

In another embodiment of the present disclosure, the monomeric unit of the novel composition is chosen from a group of catechins, preferable catechin or epicatechin.

The present disclosure also relates to a method of manufacture of the novel composition by a process illustrated in this document.

In one embodiment of the present disclosure, the standardized composition comprises optionally along with pharmaceutically acceptable excipients.

In another embodiment of the present disclosure, the excipients are selected from a group comprising additives, gums, sweeteners, coatings, binders, disintegrants, lubricants, disintegration agents, suspending agents, solvents, colorants, glidants, anti-adherents, anti-static agents, surfactants, plasticizers, emulsifying agents, flavors, viscosity enhancers and antioxidants.

In still another embodiment of the present disclosure, the composition is formulated into dosage forms like liquid, powder, capsule, tablet, injectable, patch, ointment, gel, emulsion, cream, lotion, dentifrice, spray and drop. In still another embodiment of the present disclosure, the composition is either a powder or liquid.

The present disclosure also relates to a process of obtaining a novel standardized composition derived from botanical sources, standardized to 50% to 99% of a Type A procyanidin pentamer of a flavanoid, wherein the process comprising steps of:

1. Grinding the botanical raw material to a predetermined size
2. Extraction with an organic solvent to remove unwanted toxic substances.
3. Aqueous extraction of the botanical powder with deionized water
4. Extract purification using a two stage chromatographic purification set up
5. Drying, blending and sieving to obtain the composition comprising a pentamer of a flavanoid of purity 50% to 99% as shown in FIG. 1.

The present disclosure also relates to use of the present novel composition optionally along with excipients to manufacture a medicament for the treatment and management of HIV and prevention, treatment and management of influenza viral infection. The present disclosure also relates to the use of the present composition optionally along with excipients to manufacture a medicament to treat and manage HIV infection and prevent, treat and manage influenza infection in a subject in need thereof.

The present disclosure also relates to use of the present composition optionally along with excipients to manufacture a medicament improved immunological response in a subject in need thereof. The present disclosure also relates to use of the present composition to elicit an improved immunological response in a subject in need thereof.

In still another embodiment of the present disclosure, the subjects are animals and human beings.

The present disclosure also relates to a process to manufacture a novel standardized composition derived from botanical sources, standardized to 50% to 99% of a Type A procyanidin pentamer of a flavanoid, comprising the steps of:

1. Grinding of botanical cinnamon or *litchi* pericarp or ground nutshell with red coloured seed coat
2. Extraction of the material to remove the fats and toxins and other aromatic compounds using an organic (preferably ester) solvent mainly consisting of ethylacetate, butylacetate, amylacetate or 2-ethylhexylacetate either as a single solvent or a mixture of the above solvents. This step is optional for cinnamon
3. Drying the extracted plant material to free the solvent.
4. Extraction with deionised water at pH 4 or at pH between 3.8 to 5.8 preferably at pH 4.0 Extract purification using a two stage chromatographic separation, one for polar and one for non-polar molecules
5. The adsorbed material is eluted using an alcoholic solvent
6. The eluted solvent is concentrated to a fine powder
7. The concentrated mass is diluted with water and is optionally spray dried to eliminate residual solvents.

The novel composition obtained by the above process comprises 50%-99% pentamer, 1%-35% trimer and 1%-35% tetramer and is characterized as shown in FIG. 5

The disclosure is further elaborated with the help of following examples. However, these examples should not be construed to limit the scope of the disclosure.

EXAMPLE 1

1000 gms of pulverized cinnamon powder with an average size ranging from 16 mesh size are soaked in 3000 ml of ethyl acetate and poured into an extractor having a perforated bottom sieve of the 200 mesh sieve. The bottom eluent is recycled again and again over the packed mass to achieve effective extraction for a period of about 8 hrs. The eluent is discarded and the mass is removed out of the extractor and dried in a forced draft oven at 30° C. After removal of solvent by drying, the mass was again packed in the extractor. The packed mass is extracted with 5000 ml of acidified deionised water at pH 4.0 and the extract is recycled over the bed for about 8 hrs at 35° C. to achieve efficient extraction.

The extract is filtered though a two-stage chromatographic column to obtain the composition having 80% of Type A procyanidin pentamer of flavanoid of molecular weight 1440 the extract is passed through the first column to extract the relatively less polar molecules of the composition and the second stage of chromatographic separation is for the relatively more polar molecules of the composition. The resins used were the equivalent of an XAD-1180 and an XAD-7HP resin respectively. The column was thoroughly washed with D.M. water free of adhering substances and the eluent is neutral. The column is further eluted with 175 ml pure isopropyl alcohol and the collected eluent is concentrated under vacuum below 40° C. and diluted with water and spray dried under following conditions:

Spray drier: Co current airflow
Inlet temperature: 140° C.
Outlet temperature 60° C.
Atomizer RPM 14000
The final weight is 5 gms.

EXAMPLE 2

1000 gms of pulverized cinnamon powder with an average size ranging from 16 mesh size are soaked in 3000 ml of ethyl acetate and poured in to an extractor having a perforated bottom sieve of the 200 mesh sieve. The bottom eluent is recycled again and again over the packed mass to achieve effective extraction for a period of 10 hrs. The eluent is discarded and the mass is removed out of the extractor and dried in a forced draft oven at 30° C. After removal of solvent by drying, the mass was again packed in the extractor. The packed mass is extracted with 5 liters of Acidified Deionised water at pH 4.0 the extract is recycled over the bed for about 8 hrs at 35° C. to achieve efficient extraction.

The extract is filtered though a two-stage chromatographic column to obtain a composition of 75% Type A procyanidin pentamer of flavanoid of 1440 molecular weight. First, the extract is passed through the first column to extract the relatively less polar molecules of the composition and the second stage of chromatographic separation is for the relatively more polar molecules of the composition. The resins used were the equivalent of an XAD-1180 and an XAD-7HP resin respectively. The column was thoroughly washed with D.M. water free of adhering substances and the eluent is neutral. The column is further eluted with 250 ml pure methyl alcohol and the collected eluent is concentrated under vacuum below 40° C. and diluted with water and spray dried under following conditions:
Spray drier: Co current airflow
Inlet temperature: 145° C.
Outlet temperature 60° C.
Atomizer RPM 14000
The final weight 4.5 gms

EXAMPLE 3

1000 gms of pulverized cinnamon powder with an average size ranging from 16 mesh size are soaked in 2500 ml of butylacetate and poured in to an extractor having a perforated bottom sieve of the 200 mesh sieve. The bottom eluent is recycled again and again over the packed mass to achieve effective extraction for a period of 10 hrs. The eluent is discarded and the mass is removed out of the extractor and dried in a forced draft oven at 30° C. After removal of solvent by evaporation, the mass was again packed in the extractor. The packed mass is extracted with Acidified demineralised water the extract is recycled over the bed for about 12 hrs at 30° C. to achieve efficient extraction.

The extract is filtered though a two-stage chromatographic column to obtain the composition of 89% Type A procyanidin pentamer of flavanoid having 1440 molecular weight first the extract is passed through the first column to extract the relatively less polar molecules of the composition and the second stage of chromatographic separation is for the relatively more polar molecules of the composition. The resins used were the equivalent of an XAD-1180 and an XAD-7HP resin respectively. The column was thoroughly washed with D.M. water free of adhering substances and the eluent is neutral. The column is further eluted with 200 ml pure Ethyl alcohol and the collected eluent is concentrated under vacuum below 40° C. and diluted with water and spray dried under following conditions:
Spray drier: Co current airflow
Inlet temperature: 145° C.
Outlet temperature 60° C.
Atomizer RPM 14000
Final weight 4.8 gms

EXAMPLE 4

1000 gms of pulverized cinnamon powder with an average size ranging from 16 mesh size is soaked in 2500 ml butylacetate and poured in to an extractor having a perforated bottom sieve of the 200 mesh sieve. The bottom eluent is recycled again and again over the packed mass to achieve effective extraction for a period of 10 hrs. The eluent is discarded and the mass is removed out of the extractor and dried in a forced draft oven at 30° C. After removal of solvent by evaporation, the mass was again packed in the extractor. The packed mass is extracted with 5 ltrs of acidified deionised water and the extract is recycled over the bed for about 12 hrs at 30° C. to achieve efficient extraction.

The extract is filtered though a two-stage chromatographic column to obtain the composition of 99% Type A procyanidin pentamer of flavanoid having 1440 molecular weight first the extract is passed through the first column to extract the relatively less polar molecules of the composition and the second stage of chromatographic separation is for the relatively more polar molecules of the composition. The resins used were the equivalent of an XAD-1180 and an XAD-7HP resin respectively. The column was thoroughly washed with D.M. water free of adhering substances and the eluent is neutral. The column is further eluted with pure isopropylalcohol and the collected eluent is concentrated under vacuum below 40° C. and diluted with water and spray dried under following conditions:
Spray drier: Co current airflow
Inlet temperature: 145° C.
Outlet temperature 60° C.
Atomizer RPM 14000
Final weight 5 gms

EXAMPLE 5

1000 gms of pulverized cinnamon *cassia* powder with an average size ranging from 16 mesh size are soaked in 3000 ml of ethyl acetate and poured into an extractor having a perforated bottom sieve of the 200 mesh sieve. The bottom eluent is recycled again and again over the packed mass to achieve effective extraction for a period of about 8 hrs. The eluent is discarded and the mass is removed out of the extractor and dried in a forced draft oven at 30° C. After removal of solvent by drying, the mass was again packed in the extractor. The packed mass is extracted with 5000 ml of acidified deionised water at pH 4.0 and the extract is recycled over the bed for about 8 hrs at 35° C. to achieve efficient extraction.

The extract is filtered though a two-stage chromatographic column to obtain the composition having 55% of Type A procyanidin pentamer of flavanoid of molecular weight 1440 the extract is passed through the first column to extract the relatively less polar molecules of the composition and the second stage of chromatographic separation is for the relatively more polar molecules of the composition. The resins used were the equivalent of an XAD-1180 and an XAD-7HP resin respectively. The column was thoroughly washed with D.M. water free of adhering substances and the eluent is neutral. The column is further eluted with 175 ml pure isopropyl alcohol and the collected eluent is concentrated under vacuum below 40° C. and diluted with water and spray dried under following conditions:
Spray drier: Co current airflow
Inlet temperature: 140° C.
Outlet temperature 60° C.
Atomizer RPM 14000
The final weight is 2.5 gms.

EXAMPLE 6

Extraction from Litchi Dried Pericarp 1000 gms of pulverized dried litchi pericarp is soaked in 5000 ml of volume of acidulated water for 12 hrs time and filtered clear. The clear filtrate is passed through a column containing adsorbent resin equivalent to XAD-1140 and an XAD-7HP to trap the polar and relatively nonpolar compounds. The first column being the nonpolar one is eluted with ethyl alcohol and the eluent concentrated to get a free flowing powder yield 500 mgms. The second column which contains all the polar substances gets eluted with ethyl alcohol separately and concentrated to get 1 gm of powder. On HPLC analysis, this fraction showed 85% Type A procyanidin pentamer of flavanoid of molecular weight 1440.

EXAMPLE 7

Extraction from Ground Nut Shell Along with Red Skin of the Ground Nut Seed 1000 gms of dried ground nut shell along with the red skin on the seed is soaked in 5000 ml of volume of acidulated water at pH 3.8 for 48 hrs and is then filtered to a clear liquid. The clear filtrate is passed through a column containing adsorbent resin equivalent to XAD-1140 and an XAD-7HP to trap the polar and relatively non polar compounds. The first column being the non polar one is eluted with ethyl alcohol and the eluent concentrated to get a free flowing powder of yield 20 gms. The second column which contains all the polar substances gets eluted with ethyl alcohol separately and concentrated to a 500 mg powder. On HPLC analysis, this fraction showed 82% Type A procyanidin pentamer of flavanoid of molecular weight 1440 as shown in FIG. 5.

EXAMPLE 8

Purification to Obtain Pentamer of Flavanoid

The powder isolated by the procedure detailed in Examples 1-6, is dissolved in 200 volumes of water and filtered clear. The clear filtrate is treated with activated charcoal to decolorize the solution at 60° C. and filtered clear on filter paper to remove all insoluble particles. The filtered solution thus obtained is extracted with ethyl acetate twice to remove all solvent soluble and concentrated to get a powder. The powder was subjected column chromatography on reverse phase C-18 silica gel using 0.1% aqueous formic acid and 0.1% methanolic formic acid in gradient manner in flash chromatograph using the following parameters.

Equipment: Combiflash Companion with variable UV detector
Column: Redisep 12 gms (Reverse Phase Silica)
Detection wavelengths: 254 nm and 280 nm
Flowrate: 18 ml/min
Peak Tube volume: 18 ml/min
Peak width: 1 min
Threshold: 0.20 AU
Solvent A: 0.1% Aq. Formic acid
Solvent B: 0.1% Formic Acid in Acetonitrile Fraction numbers 1 to 19 were discarded. Fraction numbers 20 to 22 were pooled and concentrated to get 256 gms of pale brown coloured powder. The resultant powder on TLC screening solvent system 0.1 M Sodium acetate: Acetonitrile=7:3 ratio showed a UV absorbing spot at 0.75 Rt on spraying with Anisaldehyde/sulfuric acid reagent showed Orange color spot which is thought to be characteristic of proanthocynidins.

Figure 2:
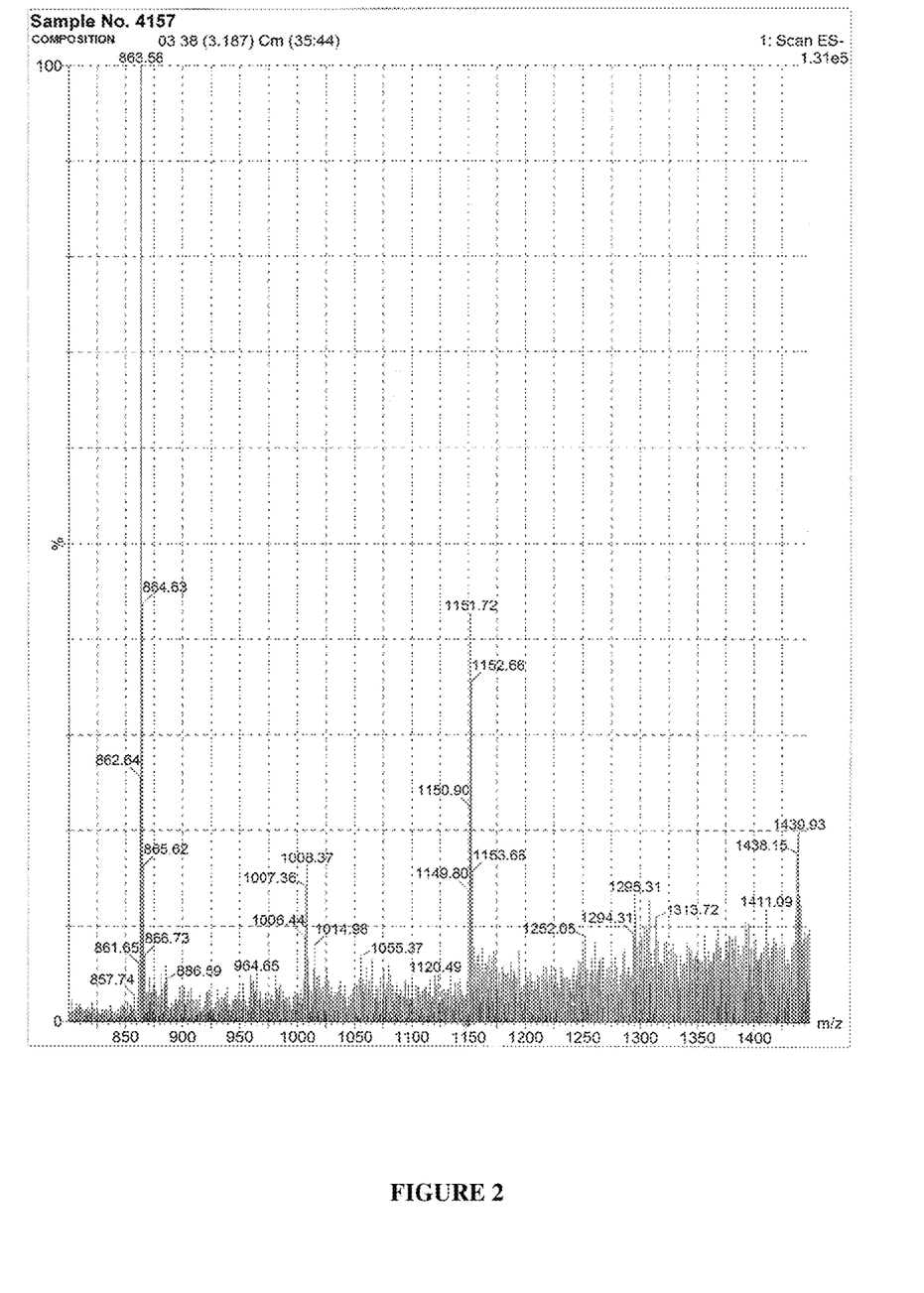
Figure 3:
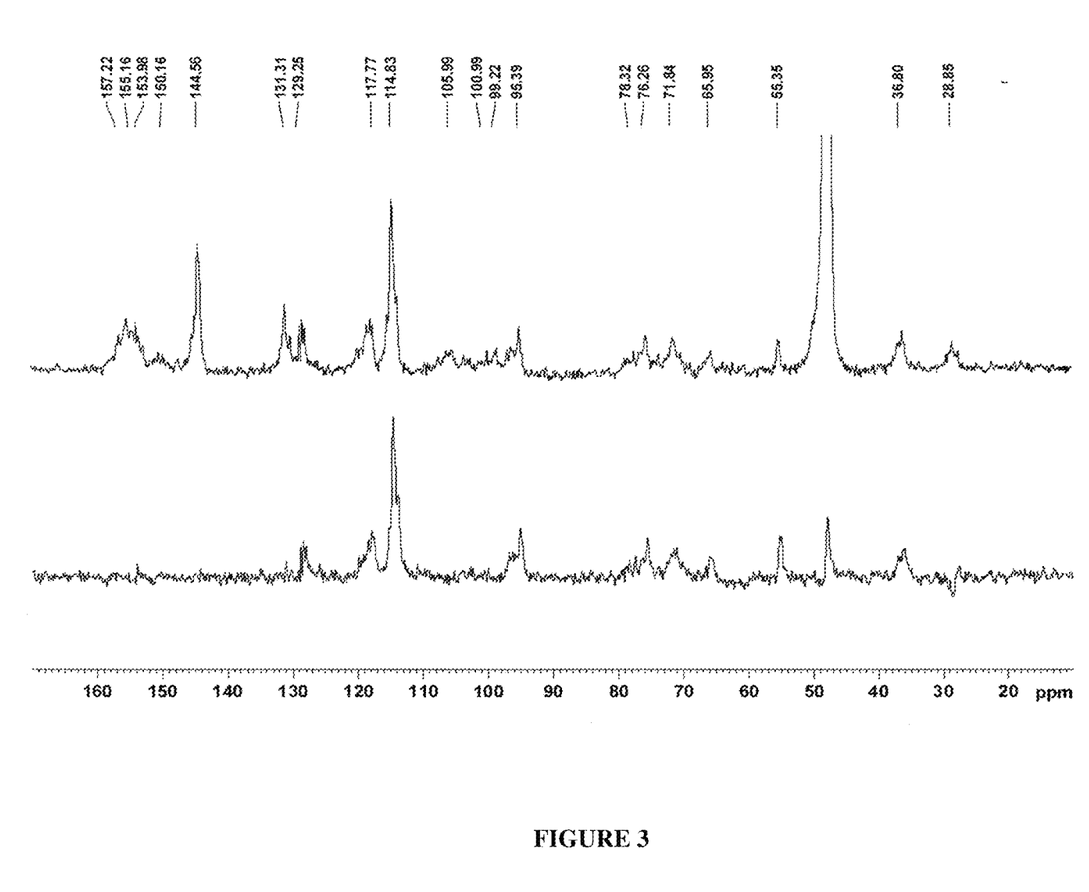
Figure 4:
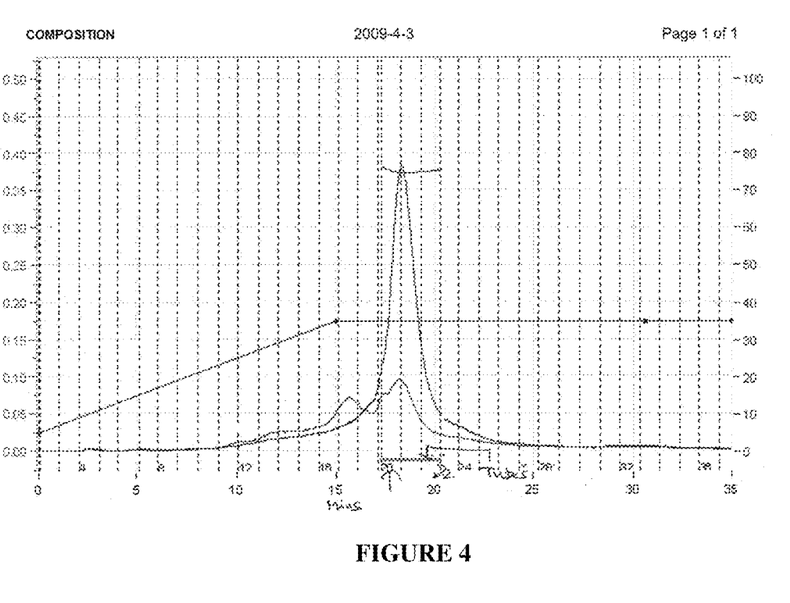

The El-MS (M-H) (as shown in FIG. 2) Ion peak at m/z 1439.9 corresponding to a multi compartment of catechin constitution (multiples of 288) corresponding to a total of five units. The molecular weight of the isolated compound is 1440.9. The configuration of the catechin units were in line with that of Epicatechin which was confirmed by the coupling pattern. The two signals between $\delta 4.84$ to 4.91 four signals of singlet (peak broadening due to high molecular weight oligomer) of 2,3 cis stereochemistry in the flavan-3-ol unit. The signals of the F-ring at 4 position of the end unit Terminal ring-CH2-methylene protons were observed between $\delta 2.6$ to 2.9 m peak broadening observed due to high molecular weight oligomeric nature. Aromatic region signals were between $\delta 6.6$ to 7.6 as two systems with respect to rings B and E. The 13C carbon signals seen at $\delta 100.9$ confirming to the C2 carbon and $\delta 27.9$ of C4 carbon the top ring C confirms the double linkage to the middle system ring as shown in FIG. 3.

Composition comprising pentameric procyanidin flavonoid of concentration ranging from about 55% w/w to about 99% w/w, trimers and tetramers each at a concentration ranging from about 0.5% w/w to about 35% w/w, optionally along with pharmaceutically acceptable excipients is obtained by following the examples 1 to 8 as recited above. In addition, the composition was used for in-vitro and in-vivo activities recited below under examples 9 to 14.

EXAMPLE 9

Effect of Test Composition on the Humoral Antibody Titre in a Subject Treated with Cyclophophamide (Immune Compromised)

Swiss albino mice of either sex were divided into 5 groups with six animals per group based on the treatment they received.

On Day 0, all five groups were sensitized with Sheep Red Blood Cells (SRBCs) containing $1 \times 10\ 8$ cells in normal saline. Groups 2-5 were treat with standard drugs and test composition combinations for 8 days (Day 0 to Day 7). On Day 7, blood samples were collected from each mouse in the five groups by retro orbital puncture for the determination of primary antibody titre. Subsequently on day 7, after the blood withdrawal, the mice were challenged with 0.1 ml of SRBCs into the foot pad. On Day 14, blood samples were collected from each mouse by retro orbital puncture for the determination of secondary antibody titre.

The results of this test are as follows:

| GROUP | TREATMENT | PRIMARY HA TITRE ON DAY 7 | SECONDARY HA TITRE ON DAY 14 |
|---|---|---|---|
| 1 | Control | 5.33 | 13.33 |
| 2 | Cyclophosphamide 25 mg/kg p.o | 0.33 | 6.67 |
| 3 | Cyclophosphamide (25 mg/kg) + Test Composition (10 mg/kg) p.o | 0.33 | 13.33 |
| 4 | Cyclophosphamide (25 mg/kg) + Test Composition (25 mg/kg) p.o | 12 | 34.66 |
| 5 | Cyclophosphamide (25 mg/kg) + Test Composition (50 mg/kg) p.o | 13.33 | 40 |

Humoral immunity serves as the first line of defense and protects the host against infection. An elevated humoral immunity renders a greater protection against infectious pathogens. The response of an individual to an antigen varies and is dependent on numerous factors including the genetic makeup and history of the individual. Cyclophosphamide is a drug which suppresses the immune system. By using this drug, all the animals evaluated in this study can be judged on their response to the antigen.

As shown in the table above, the test composition reflected an increase in the primary and secondary antibody titres of an immune compromised subject. There is a multi-fold increase in the primary and secondary antibody titres (humoral immunity). This immunological response is mounted in response to the presence of the antigen, SRBCs and takes into account the variability in immunological responses due to the pre-treatment with cyclophosphamide.

EXAMPLE 10

Effect of Test Composition on Peritoneal Macrophage, Phagocytic Activity of Blood Polynuclear Cells Mounting an immunological response to an antigen, while effective, requires further evaluation to determine the effectiveness of this attack. The effectiveness is evaluated by the immunological response's ability to eliminate the pathogen. This is determined by evaluating the phagocytic ability of the response.

Swiss Albino mice of either sex were divided into 3 groups, with six animals in each group. Single doses of the control and the test composition were given to each of the 3 groups.

Each group was treated for a period of 20 days and on the $21^{st}$ day they received 5 ml of cold phosphate buffer saline (PBS) intraperitoneally. Subsequently, the peritoneal fluid was collected and the macrophage numbers were counted using a WBC square in a haemocytometer. The cell count was estimated per cubic millimeter. The remaining mice were kept continuously treated till Day 28 and on Day 29, blood was drawn from the retro orbital plexus. Two drops of blood drawn from each mouse was placed on a slide and allowed to clot and then was placed in a moist chamber maintained at 37 C for 25 mins. These adherent cells were incubated with *Candida albicans* spores suspension and observed by staining. Subsequently the number of cells which had ingested the candidial suspension was counted.

The phagocytic index and the % phagocytosis were calculated using the following formula:

$$\text{Phagocytic Index} = \frac{\text{Total no. of Candida in 100 PMN cells}}{\text{No. of PMN cells involved in Phagocytosis}}$$

% Phagocytosis = No. of PMN cells that have ingested Candida out of every 100 cells observed The above steps were carried out and the results tabulated:

| GROUP | TREATMENT | PERITONEAL MACROPHAGES | PHAGOCYTIC ACTIVITY OF THE PMN CELLS | |
|---|---|---|---|---|
| | | | Average no. of Candida/PMN | PMN showing phagocytosis |
| 1 | Control | 3558 ± 1361 | 2.185 ± 0.34 | 81 ± 3.88 |
| 2 | Test Composition g (25 mg/kg) | 4300 ± 1241 | 2.73 ± 0.37 | 95 ± 2.73 |
| 3 | Test Composition (50 mg/kg) | 7758 ± 1512 | 0.48 | 92 ± 2.48 |

The above results show an increase in peritoneal macrophage count and phagocytic activity. The increased macrophage number is a direct indication of an enhanced immunological response to the antigen. Additionally the increased phagocytic activity of these macrophages is evidence of their effectiveness against an antigen

EXAMPLE 11

Effect of Test Composition on Host's Resistance Against *E-coli* Induced Abdominal Sepsis Swiss Albino mice of either sex were divided into 3 groups and treated with the control and test composition. Single doses were administered to the mice for 28 days. On the $29^{th}$ day, the mice were injected intraperitoneally with an *E. coli* suspension containing $2.5 \times 10^9$ in PBS. The mice were observed for mortality for 24 hours post injection. The observed mortality is due to the *E. coli* infection and is also called sepsis. The animals that survived were further observed for 7 days for mortality.

The results of this experiment are tabulated below:

| GROUP | TREATMENT | MORTALITY AT 24 HOURS |
|---|---|---|
| 1 | Control | 8/8 |
| 2 | Test Composition at 10 mg/kg | 8/8 |
| 3 | Test Composition at 50 mg/kg | 3/8 |

As seen from the above results, the mortality with the control and the lower dose of the test composition was 100%. At a dose of 50 mg/kg of the test composition the mortality reduced by 63%. Only 3 out of the 8 mice died as compared to all 8 dying in the other two groups. Also no further mortality was observed in this $3^{rd}$ Group.

This shows the prophylactic effect of the test composition to the host. Pre-treatment with the test composition decreased the mortality of the mice exposed to a pathogen. This confirms the ability of the test composition to prevent infection by pathogens including bacteria and viruses.

This prevention of infection is due to the improved immunological response elicited by the composition in the presence of a pathogen. This response enables the host to control the numbers of the pathogen, thereby preventing infection.

EXAMPLE 12

Inhibition of the Influenza A (H1N1 & H3N2) Virus

This example shows the efficacy of the test composition to inhibit the H1N1 and the H3N2 viruses and hence establishes it effectiveness as a method of treatment, prevention and management of this viral infection.

Madin-Darby canine kidney (MDCK) cells ($3\times10^5$ cells per well) were inoculated into 6-well plates one day before infection with the H1N1 and H3N2 virus. Three days later, cells were infected with serially diluted H1N1 and H3N2 viruses for 1 hour before 3 mL overlay medium was added into each well. After forty hours, the cells were fixed with 10% formalin for 1 hour and stained with 1% crystal violet for 15 minutes. The virus titers were determined according to the plaques counted.

The susceptibility of viruses to compounds was determined by plaque reduction assay. The procedures were similar to plaque assay except that indicated amounts of compounds were added into the overlay medium. The percentage of inhibition was calculated as $[100-(V_D/V_D)]\times100\%$, where $V_D$ and $V_C$ refer to the virus titer in the presence and absence of the compound, respectively. The minimal concentration of compounds required to reduce 50% of plaque numbers ($EC_{50}$) was calculated by regression analysis of the dose-response curves generated from plaque assays.

|  | Sensitive strain (676) | Resistant strain (6706) |
|---|---|---|
|  | Test Composition (ug/mL) | |
| 0 | 78.5 | 11 |
| 25 | 40 | 7 |
| 50 | 25.5 | 3.5 |
| EC50 | 25.5 (17.7 nM) | 36.1 (25 nM) |
|  | Tamiflu (nM) | |
| EC50 | 4.5 | >5000 |

|  | Test Compound (µg/mL) H3N2 | |
|---|---|---|
|  | PFU | Inhibit rate(%) |
|  | 141.67 | 0 |
|  | 110.33 | 22.11 |
|  | 57.33 | 59.53 |
|  | 27.67 | 80.47 |
| IC50 | 43.64 | |

From the above tabulation it is clear that the test composition it is evident that the infected cells treated with Test Composition showed a remarkable reduction in plaque formation. Additionally, the test composition was shown to be highly effective against the Tamiflu resistant strain of H1N1 hence proving its effectiveness as a potential treatment of Influenza ($H_1N_1$) viral infection. Also the $2^{nd}$ table shows the test compounds effectiveness in inhibiting the H3N2 strain of the Influenza A virus as well.

EXAMPLE 13

Effect of Test Composition on PBMC Stimulated HIV-1 (X4 Tropic Virus and R5 Tropic Virus)

HIV-1 (HXB2-X4 tropic) virus was obtained 48 hours after transfecting HXB2 molecular clone to 293T Cells. Virus titer was detected by real-time PCR. Virus was then infected to phytohemagglutinin (PHA)-stimulated Peripheral Blood Mononuclear Cell (PBMC) in 24 wells. After 16-18 hours, PBMC were washed with phosphate buffer solution (PBS) and fresh Roswell Park Memorial Institute (RPMI) medium with 2% Fetal Bovine Serum (FBS) were added. Harvest cells and virus soup at 3, 5 and 7 day post-infection (dpi).

The test composition and 3 standard drugs (AZT, AMD3100 and Tak-779), was tested in phytohemagglutinin (PHA-2 µg/mL) stimulated PBMC cells transfected with HXB2 HIV-1 virus (X4 virus and R5 virus). Multiplicity of Infection (MOI) was found to be 0.26. Viral load detection was done by RT-PCR as described above on day 3, day 5 and day 7 post-infection.

AMD3100 exhibited inhibitory activity only against CXCR4 trophic virus (average $EC_{50}$=2.05 nM) whereas Tak-779 exhibited inhibitory activity only against CCR5 trophic virus (average $EC_{50}$=0.56 nM). AZT exhibited inhibitory activity for both CCR5 trophic and CXCR4 trophic virus. The test composition showed an $EC_{50}$ value of 22.5 µg/mL (15.625 nM) for the X4 virus and 15.5 µg/mL (10.77 nM) for the R5 virus. These values were comparable and in some cases more effective than the standard drugs used.

Examples 9-11 exhibit the immunological response properties of the test composition while Examples 12-13 show the anti viral effect of the test composition against HIV and the Influenza virus ($H_1N_1$). In combination, Examples 9-13 exhibit that the test composition operates to prevent infection by a two pronged mechanism: The enhanced immunological response can act as a protective or prophylactic option to prevent infection all together. Secondly, in case of an infection, the anti viral properties of the test composition reduces the viral load (both HIV and Influenza) thereby allowing the enhanced immunological response to resolve the infection and preventing further damage. It is important to note that this immunological response is only elicited in the presence of an antigen. This is confirmed by the fact that none of the animals showed signs of inflammation and/or other symptoms associated with an over activated immune system.

This property of the test composition makes it very amenable for long term use as a prophylactic agent to prevent infection.

The composition of instant disclosure improves immunological response not only at broad concentration ranges of composition comprising pentameric procyanidin flavonoid of concentration ranging from about 55% w/w to about 99% w/w, trimers and tetramers each at a concentration ranging from about 0.5% w/w to about 35% w/w. The efficacy of the composition in eliciting immunological response is better/extraordinary at specific concentration ranges of composition comprising pentameric procyanidin flavonoid is ranging from about 80% w/w to about 99% w/w, trimers and tetramers each at a concentration ranging from about 0.5% w/w to about 20% w/w.

EXAMPLE 14

Proof-of-Concept Study to Show the Efficacy And Safety of the Novel Composition in HIV and Aids Patients A prospective, double-blind, randomized, placebo-controlled study was conducted in 40 antiretroviral naive, asymptomatic HIV-1 infected patients. The test composition was studied in 40 antiretroviral naive, asymptomatic HIV-1 infected patients whose CD4 count between 250-500/mm³ The test composition was tested at 300 mg/day for 12 weeks and was administrated in capsule dosage form. The test composition showed a decrease in viral load by 11.29% as compared to placebo that showed an increase by 67.28%. There was a decline in CD4 count in both groups, but the percentage decrease in CD4 count in the test composition group was found half of that of placebo (7.74% in test composition as compared with 13.88% decrease in placebo). Hence, the test composition was found to be safe and efficacious with respect to most of the vital organ functions and biochemical parameters. Example 14 details the ability of the test composition to inhibit the viral load thereby confirming the anti viral effect of the test composition. Also the improvement in WBC (CD4) count when compared to the placebo is an important indication of the improving immunological response.

What is claimed is:

1. A composition comprising Type A pentameric procyanidin flavonoid of concentration ranging from about 55% w/w to about 99% w/w, trimers and tetramers each at a concentration ranging from about 0.5% w/w to about 35% w/w, optionally along with pharmaceutically acceptable excipients.

2. The composition as claimed in claim 1, wherein said composition is obtained from a plant source selected from the group consisting of *Cinnamomum, Litchi* and *Arachis*.

3. The composition as claimed in claim 1, wherein the preferable concentration of Type A pentameric procyanidin flavonoid is ranging from about 80% w/w to about 98% w/w, trimers and tetramers each at a concentration ranging from about 0.5% w/w to about 20% w/w.

4. The composition as claimed in claim 1, wherein said Type A pentameric procyanidin flavonoid is having molecular weight of about 1440 daltons.

5. The composition as claimed in claim 1, wherein said excipients are selected from the group consisting of gums, granulating agents, binding agents, lubricating agents, disintegrating agents, sweetening agents, coloring agents, flavoring agents, coating agents, plasticizers, preservatives, suspending agents, emulsifying agents, antistatic agents, and spheronization agents.

6. The composition as claimed in claim 1, wherein said composition is formulated into various dosage forms selected from the group consisting of tablet, troches, lozenges, aqueous or oily suspensions, dispersible powders or granules, emulsion in hard or soft gel capsules, syrups and elixirs.

7. A process for preparation of composition comprising Type A pentameric procyanidin flavonoid of concentration ranging from about 55% w/w to about 99% w/w, trimers and tetramers each at a concentration ranging from about 0.5% w/w to about 35% w/w, said process comprising steps of:
a) extracting pulverized plant mass using organic solvent to remove toxic substances;
b) drying the mass to remove the organic solvent;
c) re-extracting the dried mass using aqueous solvent to obtain extract; and
d) purifying the extract through chromatographic column followed by concentrating, purifying, standardizing and drying to obtain the composition.

8. The process as claimed in claim 7, wherein the pulverized plant mass is selected from the group of plants consisting of *Cinnamon, Litchi* and *Arachis*.

9. The process as claimed in claim 7, wherein the organic solvent is selected from the group consisting of ethylacetate, butylacetate, amylacetate, 2-ethylhexylacetate and any combinations thereof.

10. The process as claimed in claim 7, wherein said extraction is carried out for a time period ranging from about 8 hours to about 12 hours, preferably for about 10 hours.

11. The process as claimed in claim 7, wherein said toxic substances include coumarin and aldehydes.

12. The process as claimed in claim 7, wherein said extract is filtered through two stage chromatographic column.

13. The process as claimed in claim 7, wherein said chromatographic columns are selected from the group consisting of XAD-1180, XAD-7HP and XAD-1140 resins.

14. The process as claimed in claim 7, wherein said re-extraction with aqueous solvent is carried out at a pH ranging from about 3.8 to about 5.8, preferably at about 4.0.

15. The process as claimed in claim 7, wherein said re-extraction is carried out for a time period ranging from about 8 hours to about 12 hours, preferably for about 10 hours at a temperature ranging from about 30° C. to 90° C., preferably ranging between 31° C. to 40° C.

16. The process as claimed in claim 7, wherein said aqueous solvent is acidified deionised water.

17. The process as claimed in claim 7, wherein said composition further comprising of excipients selected from the group consisting of gums, granulating agents, binding agents, lubricating agents, disintegrating agents, sweetening agents, coloring agents, flavoring agents, coating agents, plasticizers, preservatives, suspending agents, emulsifying agents, antistatic agents, and spheronization agents.

18. A method to improve immunological response in a subject in need thereof, said method comprising step of administering pharmaceutically effective amount of composition comprising Type A pentameric procyanidin flavonoid of concentration ranging from about 55% w/w to about 99% w/w, trimers and tetramers each at a concentration ranging from about 0.5% w/w to about 35% w/w, optionally along with pharmaceutically acceptable excipients to the subject.

19. The method as claimed in claim 18, wherein the immunological response is improved in diseases selected from the group consisting of influenza, HIV infection and AIDS.

20. The method as claimed in claim 18, wherein the immunological response is improved in a subject in need thereof.

21. The method as claimed in claim 18, wherein the pharmaceutically effective amount of composition is ranging from about 1 mg/kg to about 100 mg/kg body weight of the subject.

22. The method as claimed in claim 18, wherein said method is used in treatment, and management of infection caused by a pathogen in the subject.

23. The method as claimed in claim 22, wherein said pathogen includes influenza A virus and HIV viruses.

24. The method as claimed in claim 23, wherein said virus types are Influenza viruses H1N1 and H3N2.

25. The method as claimed in claim 23, wherein said virus types are HIV X4 and R5 tropic viruses.

26. The method as claimed in claim 18, wherein the subject is an animal or human being.

27. A method of treating, and managing a viral infection in a subject in need thereof, wherein said method comprising step of administering pharmaceutically effective amount of a composition comprising Type A pentameric procyanidin flavonoid of concentration ranging from about 55% w/w to about 99% w/w, trimers and tetramers each at a concentration ranging from about 0.5% w/w to about 35% w/w, optionally along with pharmaceutically acceptable excipients as an antiviral preparation to the subject.

28. The use method as claimed in claim 27, wherein said composition inhibits a virus selected from the group consisting of influenza A virus, X4 tropic of HIV and R5 tropic virus of HIV.

29. The method as claimed in claim 27, wherein the pharmaceutically effective amount of composition is ranging from about 1 mg/kg to about 100 mg/kg body weight of the subject.

30. The method as claimed in claim 27, wherein the subject is an animal or human being.

31. A method of treating, and managing a retroviral infection in a subject in need thereof, said method comprising step of administering pharmaceutically effective amount of composition comprising Type A pentameric procyanidin flavonoid of concentration ranging from about 55% w/w to about 99% w/w, trimers and tetramers each at a concentration ranging from about 0.5% w/w to about 35% w/w, optionally along with pharmaceutically acceptable excipients to the subject.

32. The method as claimed in claim 31, wherein said retroviral infection is selected from the group consisting of Influenza A infection, HIV infection and AIDS.

33. The method as claimed in claim 31, wherein the pharmaceutically effective amount of composition is ranging from about 1 mg/kg to about 100 mg/kg body weight of the subject.

34. The method as claimed in claim 31, wherein the subject is an animal or human being.

* * * * *